(12) United States Patent
Muessig et al.

(10) Patent No.: US 11,110,286 B2
(45) Date of Patent: Sep. 7, 2021

(54) DELIVERY SYSTEM FOR AN IMPLANTABLE MEDICAL DEVICE

(71) Applicant: BIOTRONIK SE & Co. KG, Berlin (DE)

(72) Inventors: Dirk Muessig, West Linn, OR (US); Larry Stotts, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 228 days.

(21) Appl. No.: 16/384,214

(22) Filed: Apr. 15, 2019

(65) Prior Publication Data

US 2019/0240493 A1 Aug. 8, 2019

Related U.S. Application Data

(63) Continuation-in-part of application No. 14/731,701, filed on Jun. 5, 2015, now abandoned.

(60) Provisional application No. 62/009,935, filed on Jun. 10, 2014.

(51) Int. Cl.
| | |
|---|---|
| *A61N 1/37* | (2006.01) |
| *A61N 1/375* | (2006.01) |
| *A61B 17/34* | (2006.01) |
| *A61N 1/372* | (2006.01) |
| *A61M 25/06* | (2006.01) |
| *A61N 1/362* | (2006.01) |

(52) U.S. Cl.
CPC ........ *A61N 1/3756* (2013.01); *A61B 17/3468* (2013.01); *A61N 1/37205* (2013.01); *A61N 1/37512* (2017.08); *A61N 1/37518* (2017.08); *A61M 25/0668* (2013.01); *A61M 2025/0675* (2013.01); *A61N 1/362* (2013.01)

(58) Field of Classification Search
CPC ............. A61F 2/011; A61F 2002/9505; A61B 17/3468; A61N 1/056; A61N 1/057; A61N 1/3756; A61N 1/37512; A61N 1/37518

See application file for complete search history.

(56) References Cited

U.S. PATENT DOCUMENTS

| | | |
|---|---|---|
| 3,835,864 A | 9/1974 | Rasor et al. |
| 4,142,531 A | 3/1979 | Magovern et al. |
| 4,582,056 A | 4/1986 | McCorkle |

(Continued)

FOREIGN PATENT DOCUMENTS

WO 2012082755 A1 6/2012

OTHER PUBLICATIONS

European Search Report and Annex to the European Search Report on European Patent Application No. EP 15 17 0074, dated Oct. 21, 2015 (8 pages).

*Primary Examiner* — Alexander J Orkin

(74) *Attorney, Agent, or Firm* — Buchanan Ingersoll & Rooney PC

(57) ABSTRACT

A delivery tool for an implantable medical device to be introduced into a human or animal body, in particular, an implantable leadless pacemaker, the delivery tool having an outer sheath and an inner sheath, wherein the inner sheath is configured to be retractable into a lumen of the outer sheath, wherein a distal side of the inner sheath is configured to provide regions which are reversibly collapsible and non-collapsible in diameter, wherein a non-collapsible region is arranged at the distal end of the inner sheath. A system including a delivery tool and an implantable medical device is also provided.

8 Claims, 3 Drawing Sheets

(56) References Cited

U.S. PATENT DOCUMENTS

| | | | |
|---|---|---|---|
| 4,946,440 A | 8/1990 | Hall | |
| 5,180,368 A | 1/1993 | Garrison | |
| 5,476,493 A | 12/1995 | Muff | |
| 5,601,600 A | 2/1997 | Ton | |
| 5,755,762 A | 5/1998 | Bush | |
| 7,232,452 B2 | 6/2007 | Adams et al. | |
| 7,776,080 B2 | 8/2010 | Bei et al. | |
| 2004/0181237 A1 | 9/2004 | Forde et al. | |
| 2005/0065589 A1 | 3/2005 | Schneider et al. | |
| 2006/0085041 A1 | 4/2006 | Hastings et al. | |
| 2006/0212042 A1 | 9/2006 | Lamport et al. | |
| 2007/0049796 A1 | 3/2007 | Fujikura | |
| 2007/0282414 A1 | 12/2007 | Soltis et al. | |
| 2008/0154296 A1 | 6/2008 | Taylor et al. | |
| 2008/0283066 A1 | 11/2008 | Delgado et al. | |
| 2009/0054803 A1 | 2/2009 | Saadat et al. | |
| 2010/0286791 A1* | 11/2010 | Goldsmith | A61B 17/0057 623/23.7 |
| 2011/0190862 A1* | 8/2011 | Bashiri | A61F 2/95 623/1.11 |
| 2012/0130395 A1* | 5/2012 | Vardi | A61B 17/221 606/127 |
| 2012/0165827 A1* | 6/2012 | Khairkhahan | A61B 17/221 606/129 |
| 2013/0131693 A1 | 5/2013 | Berthiaume et al. | |
| 2013/0178888 A1 | 7/2013 | Bliss et al. | |
| 2013/0253343 A1 | 9/2013 | Waldhauser et al. | |
| 2014/0378991 A1* | 12/2014 | Ollivier | A61N 1/37205 606/129 |
| 2016/0015983 A1* | 1/2016 | Sheldon | A61N 1/371 606/129 |

* cited by examiner

DELIVERY SYSTEM FOR AN IMPLANTABLE MEDICAL DEVICE

CROSS-REFERENCE TO RELATED APPLICATIONS

This patent application is a continuation-in-part of co-pending U.S. patent application Ser. No. 14/731,701, filed Jun. 5, 2015, which claims the benefit of U.S. Provisional Patent Application No. 62/009,935, filed on Jun. 10, 2014, the entire disclosures of which are hereby incorporated by reference in their entireties.

TECHNICAL FIELD

The present invention relates to a delivery system for an implantable medical device in a human or animal body.

BACKGROUND

The installation of implantable leadless pacemakers demands surgical procedures that employ catheter-based tooling support. Such installations widely differ from the pocket-based patient interfacing associated with the implantation of traditional lead-based pacemakers. For repositioning, and especially for explaining an implantable leadless pacemaker, a different tool has to be introduced into the body. In many cases it is desirable to introduce the pacemaker through the femoral and not the jugular vasculature, which requires a high flexibility of the catheter.

In U.S. Pat. No. 3,835,864, a delivery device is described which is used to implant an intra-cardiac stimulator through the jugularis. International Publication No. WO 2012/082755 describes a catheter system for retrieving an implantable leadless cardiac pacemaker from a patient. The catheter is not suitable for implantation of the implant.

The fixation mechanism of an implantable medical device, such as an implantable leadless pacemaker, needs to be protected during implantation. This is achieved in the prior art by using a tube (straw) like structure as a protector cup that is placed around the implantable leadless pacemaker. This tube is longer than the implantable leadless pacemaker so it extends past the fixation mechanism, such as a screw. The distal part of the tube has a soft edge to avoid damage of myocardial tissue due to applied pressure when placing the implantable leadless pacemaker. After the initial, fixation of the implantable leadless pacemaker to the myocardium, the protective tube needs to be removed to allow the implantable leadless pacemaker to move freely with the movement of the heart. The removal of the tube is achieved by sliding it back towards the atrium. During this phase, the implantable leadless pacemaker is still connected to the delivery system via a highly flexible tether. In order to assess correct placement and anchoring of the implantable leadless pacemaker, it must not interfere with any structure of the delivery system.

The combined length of the implantable leadless pacemaker implant and the protector cup is longer than the long axis of the heart. That makes it very difficult to achieve a tether mode in which the implantable leadless pacemaker can freely, undisturbed by elements of the delivery system (e.g., the protector cup), move with the myocardium, and to fully release the implantable leadless pacemaker after it is fixated into the myocardium. The required length, i.e., the combined length of the implantable leadless pacemaker and the protective tube, is longer than the distance from the apex of the right ventricle to the distal end of deflected outer sheath of the delivery device which is required to direct the implantable leadless pacemaker from a cranial direction (coming from the femoral vain) to the right ventricle.

One option is to make the implantable leadless pacemaker shorter so that the total length of the implantable leadless pacemaker and protector cup is shorter than the available working length of the long axis of the human heart. However, this solution requires increasing the diameter of the implantable leadless pacemaker because a minimum volume of the pacemaker is required for battery and electronics and, therefore, has a negative impact on the implantability due to human vessel diameter.

Another option is to move the protector cup to the outer sheath of the delivery device to allow it being retracted back into the inferior vena cava ("IVC"). However, this has the drawback that the outer sheath of the delivery device cannot be steerable and therefore does not allow the precise placement of the implantable leadless pacemaker into the target region.

The present invention is directed toward overcoming one or more of the above-mentioned problems.

SUMMARY

It is an object of the present invention to provide a delivery system for an implantable medical device that allows a more precise placement and release of the implantable medical device.

Another object is to provide a system comprising a delivery system and an implantable medical device where delivery, and recapture or explant of the medical device, can be performed.

At least these objects are achieved by the features of the independent claim(s). The other claims, the description and the drawings disclose favorable embodiments of the present invention.

A delivery system for an implantable medical device to be introduced into a human or animal body is proposed, in particular, a leadless pacemaker, having an outer sheath and an inner sheath, wherein the inner sheath is configured to be retractable into a lumen of the outer sheath, wherein a distal side of the inner sheath is configured to provide regions which are non-collapsible and reversibly collapsible in diameter, wherein a non-collapsible region is arranged at the distal end of the inner sheath.

The presented invention allows a more precise placement and release of the implantable medical device. Also, it is designed to simplify recapturing of a chronically implanted implantable leadless pacemaker during an exchange procedure due to, e.g., battery depletion. The region of collapsible diameter with the non-collapsible front end favorably acts as protector cup for the medical device.

Besides a precise placement of the medical device in the target area of the tissue in an animal or human body, a tether mode is enabled without pulling on the medical device, as well as a controlled release of the medical device. Further, more space is provided to allow an easier recapture procedure at battery depletion.

In a tether mode, the implantable medical device is released from the intimate connection to the distal delivery tool tip during the primary engagement mode of operation, but still connected via a wire or other connection elements in order to test the location and functions of the medical implant before completely releasing it from the delivery tool.

Advantageously, the present invention allows moving the protective inner sheath out of the right ventricle and the lower part of the right atrium without changing placement and direction of the outer sheath, as well as the position of the medical device. Advantageously, the fixation mechanism of the medical device, such as an implantable leadless pacemaker, can be protected during implantation. Because the inner sheath has a collapsible region at its distal side, it can safely be retracted into the lumen of the outer sheath by reducing its diameter and be pushed out of the outer sheath while expanding its diameter so that it can cover the medical device and the fixation mechanism at the distal end of the medical device, forming a protector cup for the device.

It is not necessary to make the implantable medical device shorter so that the total length (implantable medical device and protector cup) is shorter than the available working length of the long axis of the human or animal heart. Therefore, it is not required to increase the diameter of the medical device for giving a minimum volume of the medical device being required for battery and electronic components and, therefore, has no negative impact on the implantability due to human or animal vessel diameter.

It can also be avoided to move the protector cup to the outer sheath of the implant tool to allow it being retracted back into the inferior vena cava ("IVC"). Therefore, the drawback can be avoided that the outer sheath of the delivery tool cannot be steerable and, therefore, does not allow the precise placement of the medical device into the target region.

The inventive solution is to design the protective inner sheath in a way that allows it to collapse and to be pulled back into the lumen of the outer sheath. The proposed solution also allows the protective sheath to unfold back into its original shape when pushed back out of the lumen of the outer sheath. This is advantageous for repositioning procedures, in case the interface parameters (e.g., pacing threshold, sensed signal amplitude, etc.) are not acceptable for a permanent placement of the medical device, or the fixation does not appear to be stable enough to fully release the medical device from a tether mode. In addition, this delivery tool is able to support recapturing the medical device for replacement procedures when the device battery is depleted.

According to an advantageous embodiment of the delivery device, the non collapsible region may comprise a soft material configured to protect tissue while applying pressure when placing the implantable medical device. The soft distal end of the protector cup is not collapsible in diameter, but always remains in the retracted position on the outside of outer sheath, close to the distal end of it.

According to an advantageous embodiment, the collapsible region may comprise a metal structure having a memory effect, wherein the metal structure may elongate and reduce its diameter by applying a pulling force, and which may unfold the metal structure into its non-collapsed form when pushed out of the inner sheath. In particular, the metal structure may comprise Nitinol.

In an alternative embodiment, the collapsible region may comprise longitudinal sections of differing thicknesses and/or durability. In particular, in circumferential direction of the inner sheath sections of thicker material may be spaced apart by sections of thinner material.

Advantageously, the sections may comprise polymer material. By constructing the protector cup from polymers of different thicknesses and durability, small thin longitudinal sections of the protector cup can be made of the thicker material to allow for form stability while they are connected with thinner material that folds in when applying transversal force. Also, it is conceivable that the medical device itself acts as form to bring the protector cup back in its unfolded stage.

According to another aspect of the present invention, a system comprising a delivery tool and a medical implant is proposed, the medical device having a distal end and an opposing proximal end with a fastener provided for interaction with a coupling element of the delivery system, the delivery system comprising an outer sheath and an inner sheath, wherein the inner sheath is configured to be retractable into a lumen of the outer sheath, and the inner sheath being arranged to cover temporarily at least a proximal end of the implantable medical device, wherein a distal end of the inner sheath is configured to provide regions non-collapsible and reversibly collapsible in diameter.

According to an advantageous embodiment of the inventive system, the non-collapsible region may comprise a soft material configured to protect tissue while applying pressure when placing the implantable medical device. The soft distal end of the protector cup is not collapsible in diameter, but always remains in the retracted position on the outside of the outer sheath, close to the distal end of it.

According to an advantageous embodiment of the inventive system, the collapsible region may comprise a metal structure having a memory effect, wherein the metal structure elongates and reduces its diameter by applying a pulling force and which unfolds the metal structure into its non-collapsed form when pushed out of the inner sheath.

According to an alternative embodiment of the inventive system, the collapsible region may comprise longitudinal sections of differing thicknesses and/or durability.

In another embodiment, a system for delivering an implantable medical device is provided. The system may comprise a delivery catheter with an outer sheath having a distal end facing an implantation site of the implantable medical device, wherein the outer sheath comprises a distal opening at a distal end. The system may further comprise a coupling element configured to couple the implantable medical device with the outer sheath during delivery and/or recapture procedure. The system may also comprise a radially collapsible inner sheath having a distal opening, which is dimensioned to radially enclose the implantable medical device to act as protection element of the implantable medical device and which is configured to be telescoped out of the distal opening of the outer sheath to enclose the implantable medical device. Further, the system may comprise an implantable medical device with a distal tissue anchoring element and a proximal connector element, wherein the proximal connector element is configured to releasably connect to the coupling element. The outer sheath may be dimensioned such that it can slidingly receive a tether (for capturing the implantable medical device) and the inner sheath only. During delivery of the implantable medical device, the implantable medical device may be (e.g. radially) enclosed by the inner sheath while situated distal to the distal end of the outer sheath.

Further features, aspects, objects, advantages, and possible applications of the present invention will become apparent from a study of the exemplary embodiments and examples described below, in combination with the Figures, and the appended claims.

DESCRIPTION OF THE DRAWINGS

The present invention together with the above-mentioned and other objects and advantages may best be understood from the following detailed description of the embodiments, but not restricted to the embodiments, wherein is shown in.

DETAILED DESCRIPTION

Figure 1:
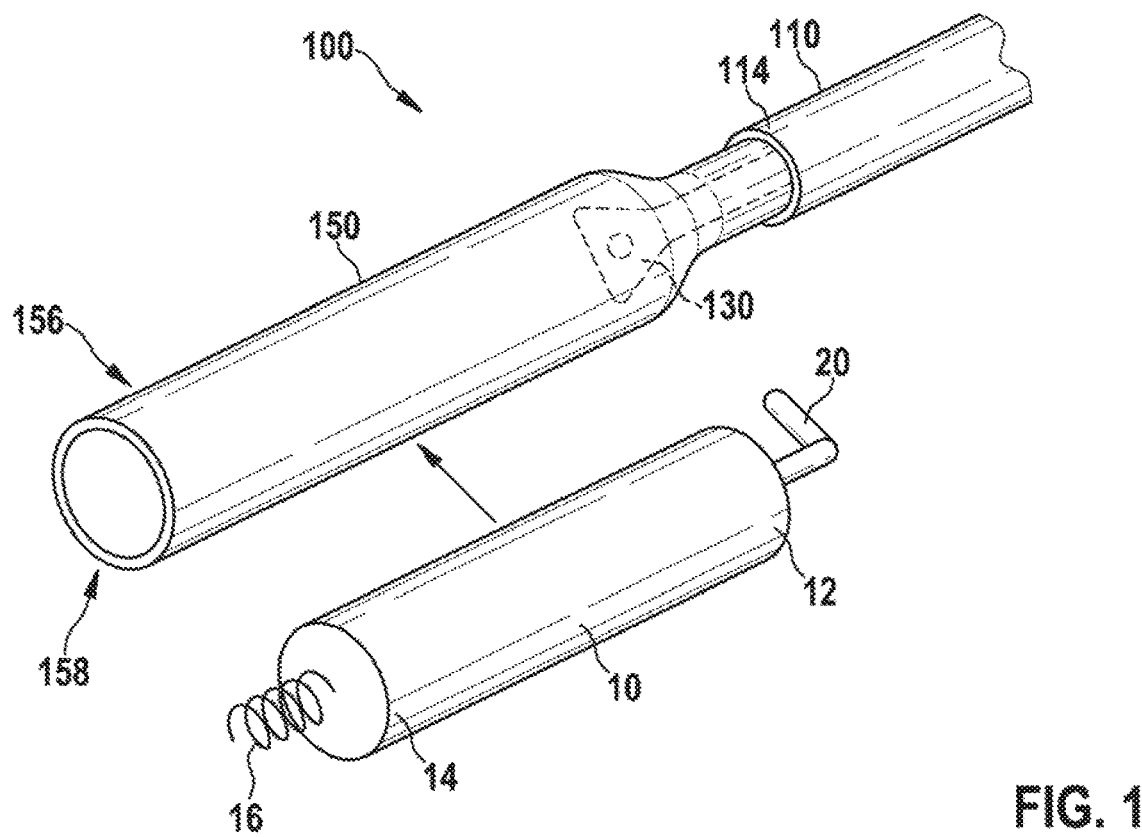
FIG. 1 shows a system comprising a delivery system and an implantable medical device having an inner sheath providing a collapsible metal structure.

In the drawings, like elements are referred to with equal reference numerals. The drawings are merely schematic representations, not intended to portray specific parameters of the invention. Moreover, the drawings are intended to depict only typical exemplary embodiments of the present invention and, therefore, should not be considered as limiting the scope of the present invention.

FIG. 1 depicts a part of a system comprising a delivery tool 100, such as, for example, a catheter, for an implantable medical device 10 (depicted lying beside the delivery tool 100) to be introduced into a human or animal body. The medical device 10 may be an implantable leadless pacemaker, having a distal end 14 and an opposing proximal end 12 with a fastener 20 provided for interaction with a coupling element 130 of the delivery tool 100.

The implantable medical implant 10 has a distal end 14 and a proximal end 12. The distal end 14 can be attached to the surrounding tissue (not shown) by means of a fixation mechanism 16 such as, for example, a helix or the like, which can be screwed into the tissue (not shown) by rotating the implantable medical device 10, or hook-like anchoring tines (not shown), which have a radially outward facing bent to hook into the tissue. The delivery tool 100 is provided to advance the implantable medical device 10 and to rotate the implantable medical device 10 or push the implantable medical device 10 against the tissue. In order to transmit torque and/or force to the implantable medical device 10, the implantable medical device 10 is intimately attached to a coupling element 130 at the distal tip of the delivery tool via a fastener 20 arranged at the proximal end 12 of the implantable medical device 10. In this embodiment, the fastener 20 is a modified flat fin, but may be a ball, a flexible neck, a generally T-shaped fastener, or the like. For the fin as fastener 20, the coupling element 130 may be a gripper or a cup protruding from a metal tip. In another embodiment, if the fastener 20 is T-shaped, the coupling element may be a tether in form of a snare, a sling, or the like.

The delivery tool 100 comprises an outer sheath 110 and an inner sheath 150, wherein the inner sheath 150 is configured to be retractable into a lumen of the outer sheath 110. The outer sheath 110 and/or the inner sheath 150 may be flexible. The outer sheath 110 comprises a lumen with a distal opening at a distal end (distal means facing to the tissue). The outer sheath 110 has an outer diameter that is less than or equal to an outer diameter of the implantable medical device 10. It is therefore not possible to retract the implantable medical device 10 into the outer sheath 110.

Hence, in the mode where the implantable medical device 10 is coupled to the coupling element 130 of the delivery tool, the implantable medical device 10 is situated distally the distal end of the outer sheath 110. The distal region of inner sheath 150 is arranged to cover temporarily the implantable medical device 10 acting as protector cup during the implant procedure. A distal end 156 of the inner sheath 150 is configured to provide collapsible and non-collapsible regions 152, 154 forming the protector cup. The coupling element 130 is attached to a torque transmitting tube or wire inside the inner sheath 150.

The non-collapsible region 154 comprises a soft material configured to protect tissue while applying pressure when placing the implantable medical device 10. The collapsible region 154 provides varying diameters of the distal side 156 of the inner sheath 150 inside and outside the outer sheath 110.

Figure 2:
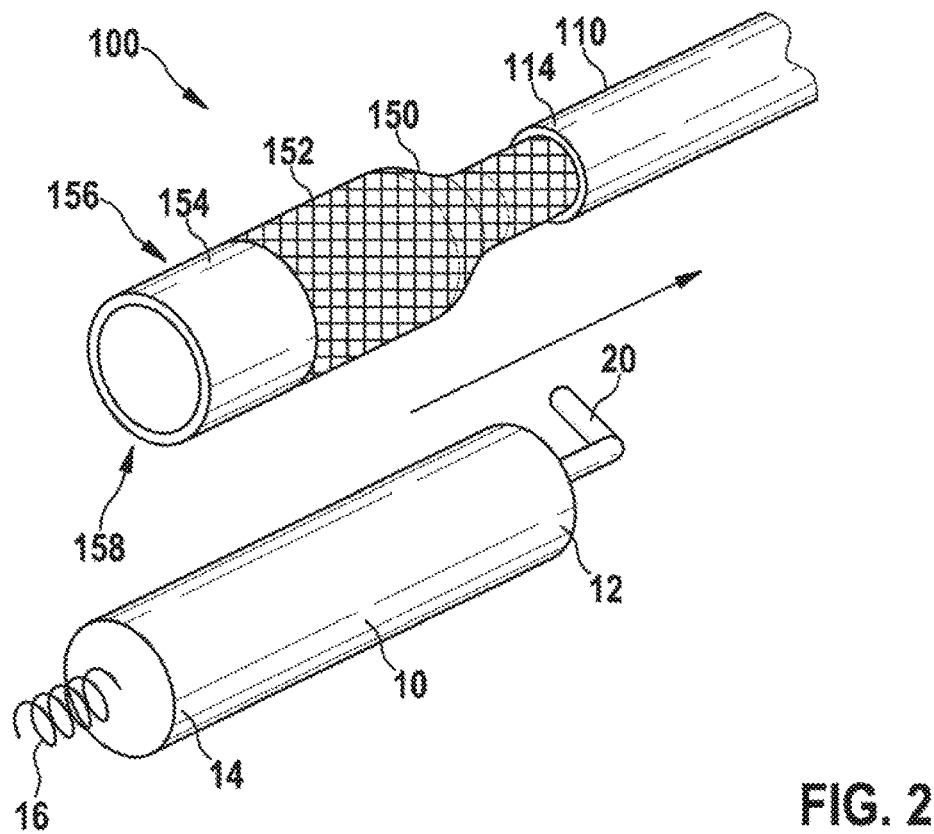
FIG. 2 shows the distal side of the delivery system of FIG. 1 showing a first embodiment of the inner sheath.

FIG. 2 illustrates the distal side of the delivery system of FIG. 1 showing a first embodiment of the inner sheath 150. Again, the implantable medical device 10 is shown lying beside the delivery device 100.

The inner sheath 150 has a soft tip 154 at its distal part 156 which is not collapsible in diameter. This non-collapsible diameter is dimensioned such that the implantable medical device 10 can fit into the distal part 156 easily or tightly, when it is coupled to the delivery device 100 and therefore situated distal to the distal end of the outer sheath 110. The inner sheath therefore extends distal to the distal end of the outer sheath 110 to cover at least partially the implantable medical device 10. A region 152 having a collapsible diameter is arranged at the proximal part of the soft tip and comprises a mesh-like structure which can be moved into the outer sheath 110. The mesh-like structure of the collapsible region 152 may be composed of, e.g., Nitinol. The collapsible region 152 comprises a metal structure having a memory effect, such that the metal structure elongates and reduces its diameter by applying a pulling force, and which unfolds the metal structure into its non-collapsed form when pushed out of the inner sheath 150.

Because of the two regions 152, 154 of the protector cup, i.e., the distal non-collapsible soft tip and the proximal collapsible structure, when the inner sheath 150 is pulled back into the outer sheath 110, the collapsible region 152 collapses in diameter and can be moved through the distal opening at the distal end into the lumen of the outer sheath 110 (indicated by an arrow in FIG. 2) while the implantable medical device 10 stays distal to the distal end of the outer sheath 110. When pushed out again, the collapsible region 152 unfolds back into its original shape thereby snuggles around the implantable medical device 10 situating distal to the distal end of the outer sheath and forms a protective element around the implantable medical device 10.

Figure 3:
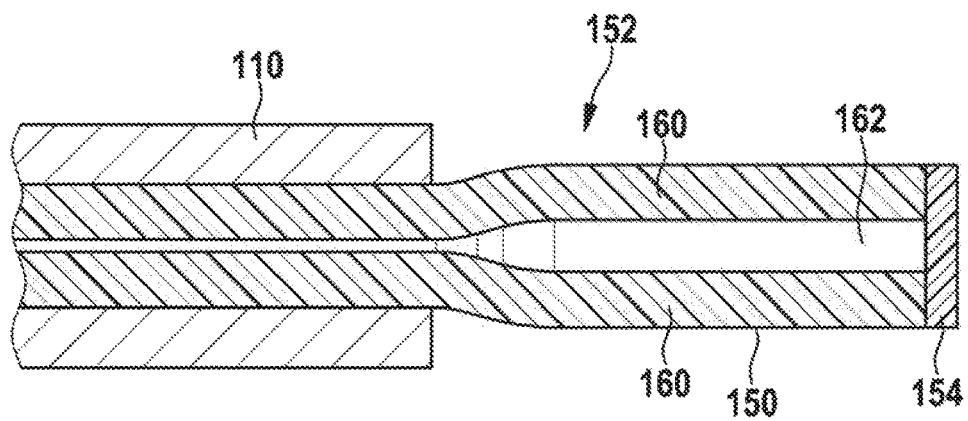
FIG. 3 shows a second embodiment of an inner sheath providing sections of different thicknesses and durability in its unfolded state outside the outer sheath and in its collapsed state inside the outer sheath.

FIG. 3 illustrates a second embodiment of an inner sheath 150 forming a protector cup providing sections of different thicknesses and durability in its unfolded state outside the outer sheath 110 and in its collapsed state inside the outer sheath 110. The collapsible region 152 comprises longitudinal sections 160, 162 of differing thicknesses and/or durability. The thicker sections 160 provide for form stability of the distal side 156 of the inner sheath 150 and are connected to each other by sections 162 of thinner material.

The protector cup may be composed of one or more polymers. The small, thin, longitudinal sections of the protector cup can be made of the thicker material 160 to allow for form stability, while they are connected with thinner material 162 that folds in when applying transversal force. The implantable medical device 10 (FIGS. 1-2) itself may act to bring the protector cup back in its unfolded stage outside the outer sheath 110.

Figure 4:
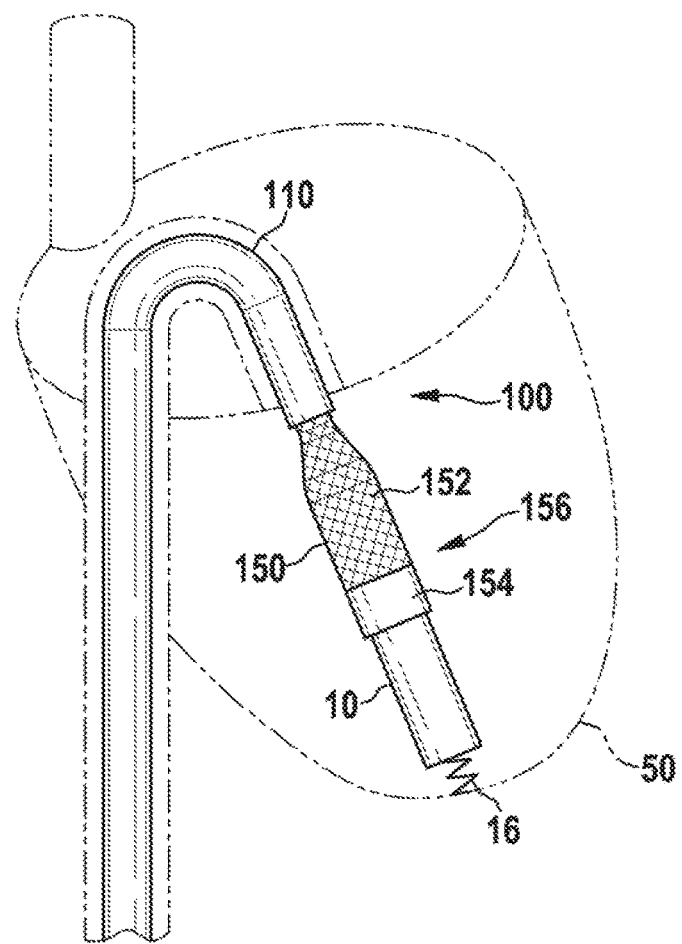
FIG. 4 shows a system comprising a delivery tool and an implantable leadless pacemaker with the implantable leadless pacemaker attached to the heart but still connected to the delivery tool.

FIG. 4 shows a system comprising a delivery tool 100 and an implantable leadless pacemaker as the medical device 10 during implant into a human or animal heart 50, with the implantable leadless pacemaker attached to the heart 50 but still connected to the delivery tool 100. Over the whole implantation procedure the implantable leadless pacemaker is situated distally to the outer sheath 110.

The fixation mechanism 16 of the implantable leadless pacemaker is protected during implantation. This is achieved using the inner sheath 150 that extends distally to the distal opening of the lumen of the outer sheath 110, and that is placed around the implantable leadless pacemaker. The distal part 156 of the inner sheath 150 has a soft edge 154 to avoid damage of myocardial tissue due to applied pressure when placing the implantable leadless pacemaker. After the initial fixation of the implantable leadless pacemaker to the myocardium, the inner sheath 150 has to be removed to allow the implantable leadless pacemaker to move freely with the movement of the heart 50. The removal of the inner sheath 150 is achieved by sliding it back towards the proximal end of the delivery tool 100 by moving it through the distal opening into the lumen of the outer sheath 110. During this phase, the implantable medical device 10 is still connected to the delivery system via a highly flexible tether, for example a snare or a sling or the like. According to the inventive delivery tool 100, the implantable medical device 10 does not interfere with any structure of the delivery tool 100 while assessing correct placement and anchoring of the implantable medical device 10.

Figure 5:
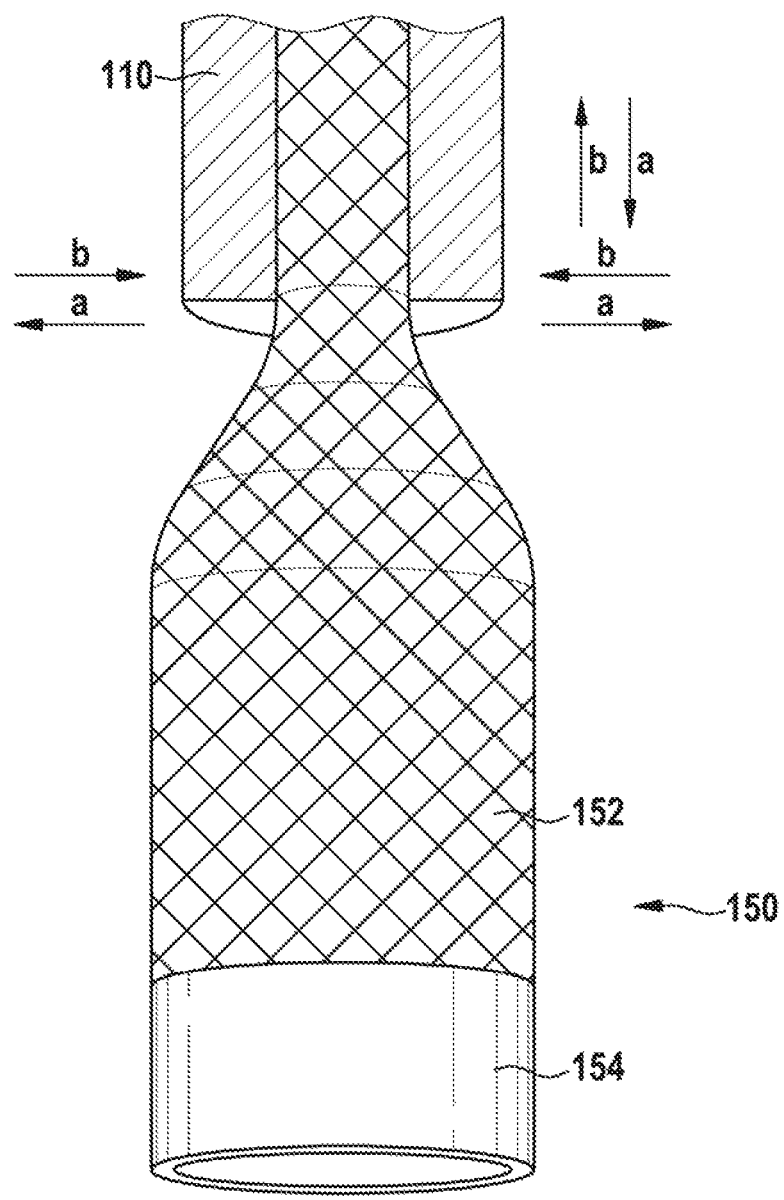
FIG. 5 shows a detail of a distal region of an inner sheath with collapsible and non-collapsible regions.

FIG. 5 depicts the change in diameter of the collapsible region 152 of the distal region 156 of the inner sheath 150 with collapsible and non-collapsible regions 152, 154, when the inner sheath 150 is retracted through the distal opening into the lumen of the outer sheath 110. Arrows labeled with the letter "b" indicate how the diameter of the inner sheath 150 collapses in the region 152 when the inner sheath 150 is moved back into the lumen of the outer sheath 110.

The inventive delivery tool 100 also allows the protective inner sheath 150 to unfold back into its original shape when pushed back out of the lumen of the outer sheath 110. This is indicated by arrows labeled with the letter "a". This is essential for repositioning procedures, in case the interface parameters (e.g., pacing threshold, sensed signal amplitude, etc.) are not acceptable for a permanent placement of the implantable medical device 10 or the fixation does not appear to be stable enough to fully release the implantable leadless pacemaker from the tether mode. In addition this mechanism, the delivery tool 100 supports recapturing the implantable leadless pacemaker for replacement procedures when the device battery is depleted.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A system comprising:
a delivery tool; and
an implantable medical device, the implantable medical device having a distal end and an opposing proximal end with a fastener provided for interaction with a coupling element of the delivery tool,
wherein the delivery tool comprises an outer sheath and an inner sheath, wherein the inner sheath is configured to be retractable into a lumen of the outer sheath, wherein a distal portion of the inner sheath is configured to provide regions which are reversibly collapsible and non-collapsible in diameter, wherein a non-collapsible region is arranged at the distal end of the inner sheath, and wherein an outer diameter of the non-collapsible region is greater than an inner diameter of the outer sheath such that the non-collapsible region remains outside of the outer sheath with the inner sheath in a retracted position and the collapsible region collapsed within the lumen of the outer sheath, and wherein the distal end of the inner sheath is configured to receive the implantable medical device.

2. The system according to claim 1, wherein the non-collapsible region comprises a soft material configured to protect tissue while applying pressure when placing the implantable medical device.

3. The system according to claim 1, wherein the collapsible region comprises a metal structure having a memory effect, wherein the metal structure elongates and reduces its diameter by applying a pulling force and which unfolds the metal structure into its non-collapsed form when pushed out of the inner sheath.

4. The system according to claim 3, wherein the metal structure comprises Nitinol.

5. The system according to claim 1, wherein the collapsible region comprises longitudinal sections of differing thicknesses and/or durability.

6. The system according to claim 5, wherein in a circumferential direction of the inner sheath sections of thicker material are spaced apart by sections of thinner material.

7. The system according to claim 5, wherein the sections comprise polymer material.

8. The system according to claim 1, wherein the collapsible and non-collapsible regions form a protective cup covering the implantable medical device during an implant procedure.

* * * * *